United States Patent
Nakajima et al.

(10) Patent No.: US 7,755,760 B2
(45) Date of Patent: Jul. 13, 2010

(54) PARTICLE COUNTER FOR MEASURING FLOATING PARTICLES WHICH CAN EFFECTIVELY REDUCE FALSE COUNTS

(75) Inventors: Yasutaka Nakajima, Tokyo (JP); Tomonobu Matsuda, Tokyo (JP)

(73) Assignee: Rion Co., Ltd., Tokyo (JP)

( * ) Notice: Subject to any disclaimer, the term of this patent is extended or adjusted under 35 U.S.C. 154(b) by 322 days.

(21) Appl. No.: 11/793,883

(22) PCT Filed: Dec. 9, 2005

(86) PCT No.: PCT/JP2005/022637

§ 371 (c)(1),
(2), (4) Date: Jun. 21, 2007

(87) PCT Pub. No.: WO2006/067977

PCT Pub. Date: Jun. 29, 2006

(65) Prior Publication Data

US 2008/0164860 A1 Jul. 10, 2008

(30) Foreign Application Priority Data

Dec. 21, 2004 (JP) ............................. 2004-368658

(51) Int. Cl.
*G01N 21/00* (2006.01)
(52) U.S. Cl. ..................... 356/338; 356/336
(58) Field of Classification Search ... 356/243.1–243.2, 356/335–343; 702/22–26
See application file for complete search history.

(56) References Cited

U.S. PATENT DOCUMENTS

| | | | | |
|---|---|---|---|---|
| 3,987,391 | A | * 10/1976 | Hogg | ........................... 377/50 |
| 6,184,983 | B1 | * 2/2001 | Yamaguchi et al. | ......... 356/335 |
| 6,784,990 | B1 | * 8/2004 | DeFreez et al. | ............. 356/338 |

FOREIGN PATENT DOCUMENTS

| | | |
|---|---|---|
| JP | 61-240143 | 10/1986 |
| JP | 09-159599 | 6/1997 |
| JP | 09-178645 | 7/1997 |
| JP | 11-271455 | 10/1999 |

* cited by examiner

*Primary Examiner*—Tarifur Chowdhury
*Assistant Examiner*—Tara S Pajoohi
(74) *Attorney, Agent, or Firm*—Carrier, Blackman & Associates, P.C.; Joseph P. Carrier; William D. Blackman

(57) ABSTRACT

A particle counter for measuring the number of floating particles contained in a sample to determine the particle concentration therein includes: a memory section for storing a relational expression between the direct current level output from a photoelectric converter when no particles exist and the frequency of occurrence of false counts; and a subtraction section for determining the frequency of occurrence of the false counts corresponding to the direct current level output from the photoelectric converter at the time of commencement of measurement with reference to the relational expression stored in the memory section and subtracting a value based on the frequency of occurrence of the false counts from a discrete value after commencement of measurement.

4 Claims, 5 Drawing Sheets

__US 7,755,760 B2__

PARTICLE COUNTER FOR MEASURING FLOATING PARTICLES WHICH CAN EFFECTIVELY REDUCE FALSE COUNTS

CROSS-REFERENCE TO RELATED APPLICATIONS

The present application is a U.S. National phase of, and claims priority based on PCT/JP2005/022637, filed 09 Dec. 2005, which, in turn, claims priority from Japanese patent application 2004-368658, filed 21 Dec. 2004. The entire disclosure of each of the referenced priority documents is incorporated herein by reference.

BACKGROUND OF THE INVENTION

1. Field of the Invention

The present invention relates to a particle counter for measuring the number of floating particles contained in a sample to determine the particle concentration therein.

2. Description of the Prior Art

So-called false counts, which are displayed as a discrete value even when no particles of measurable size exist in a sample, are obtained in a particle counter. Noise generated by a laser beam source, noise generated by a photoelectric converter, noise resulting from random voltage variation of each circuit, cosmic rays invading from the outside and the like are cited as factors for causing the false counts.

In order to reduce the noise generated by the laser beam source, a laser diode is known which is driven by a laser drive circuit which outputs a drive electric current superimposing a high-frequency component on a direct electric current to make a longitudinal mode of the laser diode a multimode (e.g., Patent Document 1).

Patent Document 1: Japanese Patent Application Publication No. 9-178645

However, according to the particle counter described in Patent Document 1, the false counts resulting from the laser diode can be reduced, but there are still problems in that the false counts resulting from other factors can be untreatable.

SUMMARY OF THE INVENTION

It is therefore an object of the present invention to provide an improved particle counter which can solve the problems stated above and can effectively reduce the false counts resulting from various factors in a relatively simple structure.

In order to attain this object, according to a first aspect of the present invention, a particle counter for measuring the number of floating particles contained in a sample to determine the particle concentration therein comprises: a memory section for storing the frequency of occurrence (hereinafter referred to as "occurrence frequency") of false counts which have been found in advance; and a subtraction section for subtracting a value based on the occurrence frequency of the false counts stored in the memory section from a discrete value after commencement of measurement.

According to a second aspect of the present invention, a particle counter for measuring the number of floating particles contained in a sample to determine the particle concentration therein comprises: a memory section for storing a relational expression between the direct current level output from a particle detecting section when no particles exist and the occurrence frequency of false counts; and a subtraction section for determining the occurrence frequency of the false counts corresponding to the direct current level output from the particle detecting section at the time of commencement of measurement with reference to the relational expression stored in the memory section and subtracting a value based on the occurrence frequency of false counts from a discrete value after commencement of measurement.

According to a third aspect of the present invention, in the particle counter of the first aspect or the second aspect, the subtraction section makes a reciprocal number (1/m) of the occurrence frequency of the calculated false counts a minimum time interval for subtraction processing and divides the measuring time by the time interval, and if the signals for increasing a discrete value in a certain time interval are generated, the subtraction section subtracts the number to be subtracted from the discrete value, while if the signals for increasing the discrete value are not generated, the subtraction section carries the number to be subtracted over to the following time interval.

BRIEF DESCRIPTION OF THE DRAWINGS

The above and other objects, features and advantages of the present invention will become more apparent from the following description when taken in conjunction with the accompanying drawings.

FIG. 4 is an output voltage wave form chart of a photoelectric converter, in which

DETAILED DESCRIPTION OF THE PREFERRED EMBODIMENTS

Figure 1:
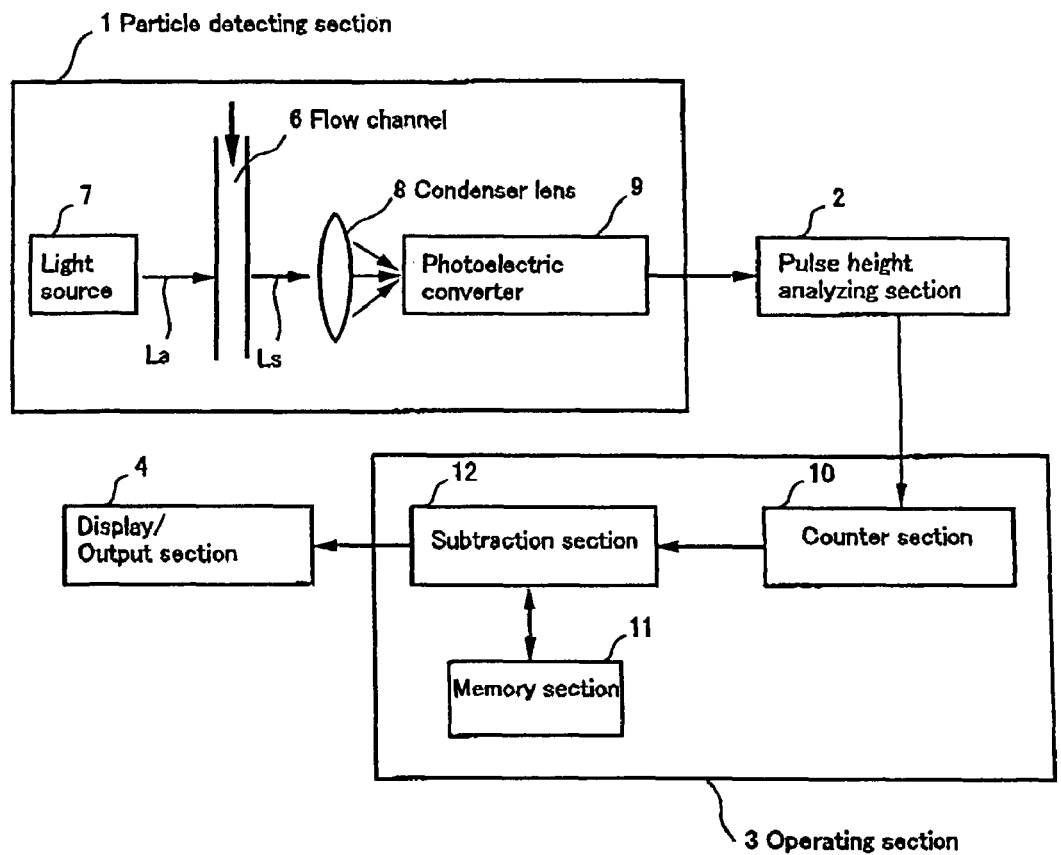
FIG. 1 is a schematic diagram of a particle counter according to a first embodiment of the present invention.
Figure 2:
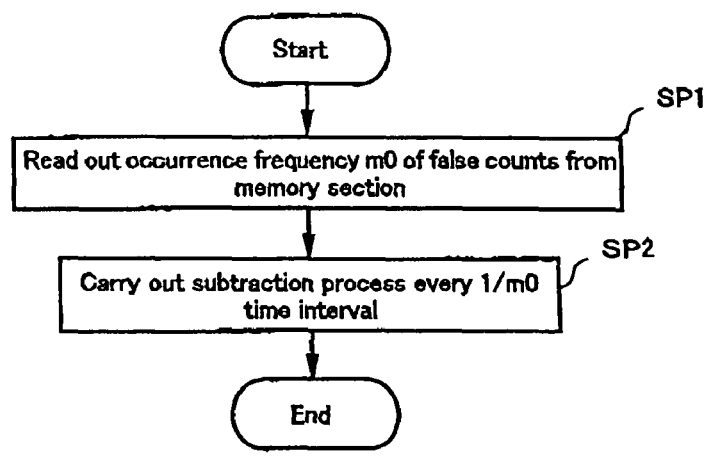
FIG. 2 is a flow chart showing the operation of the particle counter according to the first embodiment of the present invention.
Figure 3:
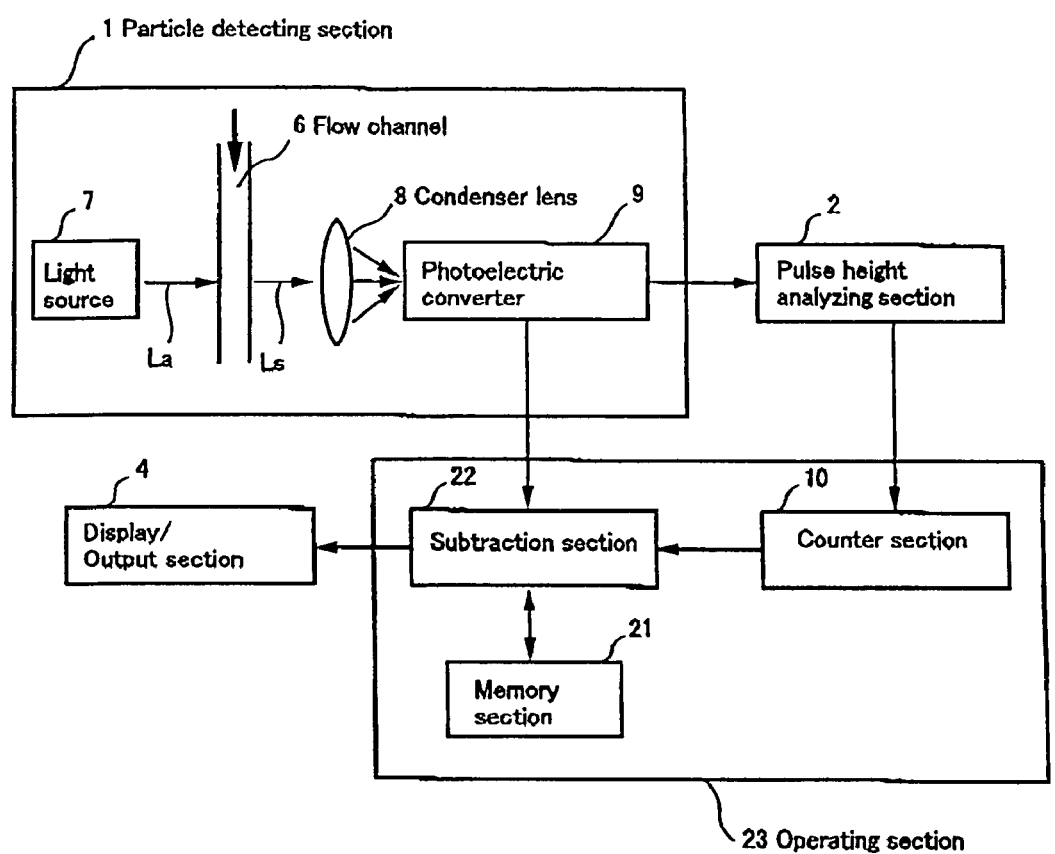
FIG. 3 is a schematic diagram of a particle counter according to a second embodiment of the present invention.
Figure 5:
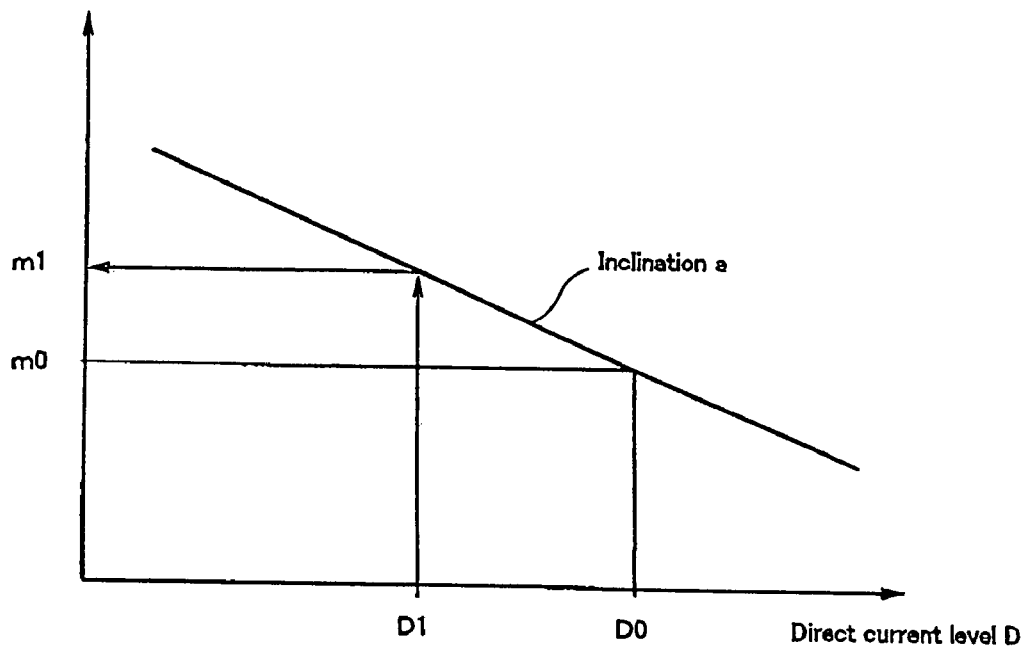
FIG. 5 is a view showing the relationship between the direct current level of the photoelectric converter and the frequency of occurrence of false counts.
Figure 6:
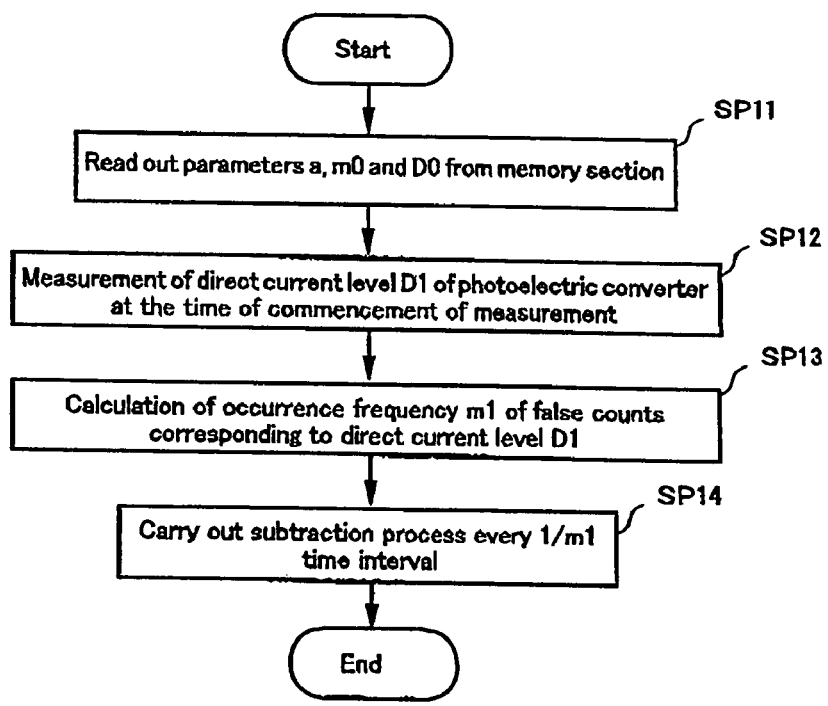
FIG. 6 is a flow chart showing the operation of the particle counter according to the second embodiment of the present invention.
Figure 7:
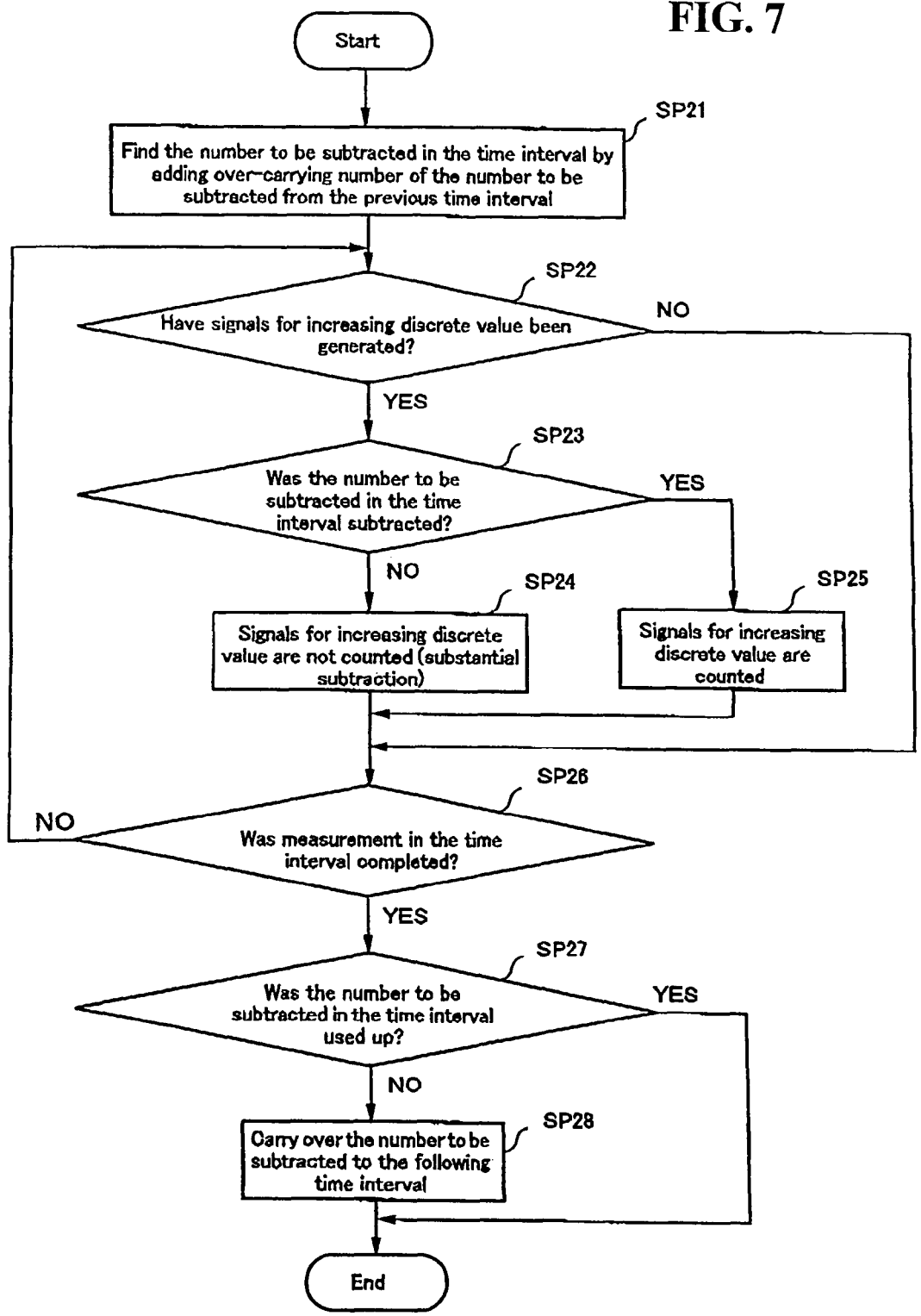
FIG. 7 is a flow chart showing the steps of a subtraction process in a certain time interval of measuring time.

A preferred embodiment of the present invention will now be described with reference to the accompanying drawings. FIG. 1 is a schematic diagram of a particle counter according to a first embodiment of the present invention, FIG. 2 is a flow chart showing the operation of the particle counter according to the first embodiment, FIG. 3 is a schematic diagram of a particle counter according to a second embodiment of the present invention, FIG. 4 is an output voltage wave form chart of a photoelectric converter, FIG. 5 is a view showing the relationship between the direct current level of the photoelectric converter and the occurrence frequency of false counts, FIG. 6 is a flow chart showing the operation of the particle counter according to the second embodiment, and FIG. 7 is a flow chart showing the steps of a subtraction process in a certain time interval of the measuring time.

A particle counter according to the first embodiment of the present invention comprises, as shown in FIG. 1, a particle detecting section 1 for detecting particles in a sample by using light, a pulse height analyzing section 2 for trapping the particles of every particle size classification, an operating section 3 for carrying out an operation taking the false counts into consideration, and a display/output section 4 for displaying the processing results of the operating section 3 or directly outputting the results as an electric signal.

The particle detecting section 1 comprises a flow channel 6 for letting a sample flow, a source of light 7 for irradiating a laser beam La onto the flow channel 6 to form a particle detecting area, a condenser lens 8 for condensing a scattered light Ls emitted from the particles passing through the particle detecting area, and a photoelectric converter 9 for converting the light condensed by the condenser lens 8 to the voltage corresponding to the intensity of light.

The pulse height analyzing section 2 receives the output signals of the particle detecting section 1 and outputs the signals above a predetermined level as a particle of the particle size corresponding to the level according to the particle size classification. A direct current level is removed from the output signals of the photoelectric converter 9 input to the pulse height analyzing section 2.

The direct current level output from the photoelectric converter 9 is a voltage corresponding to an amount of light of the background light incident on the photoelectric converter 9 in the case where there is no scattered light Ls by the particles.

The operating section 3 comprises a counter section 10 for receiving the output signals of the pulse height analyzing section 2 to count the pulse corresponding to the particle size classification, a memory section 11 for storing the occurrence frequency of the false counts at the time of shipment or production, and a subtraction section 12 for carrying out an operation so as not to increase the count value of a peak value corresponding to the minimum particle size among the number of counts output from the counter section 10 by the occurrence frequency of the false counts.

Operation of the particle counter, as constructed above, according to the first embodiment of the present invention will now be described with reference to a flow chart as shown in FIG. 2.

First, when measurement is commenced, in SP1, the subtraction section 12 reads out the occurrence frequency m0, which has been calculated and stored in advance, of the false counts at the time of shipment or production, from the memory section 11.

Next, in SP2, the subtraction process is carried out by delimitating the measuring time by the time segment of a reciprocal number 1/m0 of the occurrence frequency m0 of the false counts. This means that "1" is subtracted every 1/m0 hours relative to a discrete value of the minimum particle size output from the counter section 10. However, in the first time interval (0-½m0), subtraction is not carried out, but the discrete value of the counter section 10 is directly output to the display/output section 4 as the measurement results.

After ½m0 hours has lapsed since commencement of measurement, "1" is subtracted every 1/m0 hours. In the case where the subtraction process is not carried out in the time interval, the number to be subtracted is carried over to the following time interval for accumulation.

For example, when the signals for increasing the discrete value are input to the counter section 10, the counter section 10 counts the signals. However, in the subtraction section 12, if the signals are a count value corresponding to the minimum particle size, a process so as not to increase the discrete value by the number to be subtracted is carried out and as a result, the same effect as the subtraction can be brought about.

In this manner, if the particle counter is used under substantially the same conditions as the use conditions at the time of shipment or production, a more precise discrete value can be obtained by carrying out the subtraction based on the occurrence frequency m0 of the false counts calculated under the use conditions at the time of shipment or production.

Next, a particle counter according to a second embodiment of the present invention comprises, as shown in FIG. 3, a particle detecting section 1 for detecting particles contained in a sample by using light, a pulse height analyzing section 2 for trapping the particles of every particle size classification, an operating section 23 for carrying out an operation taking the false counts in consideration, and a display/output section 4 for displaying the processing results of the operating section 23 or directly outputting the results as an electric signal.

The operating section 23 comprises a counter section 10 for receiving the output signals of the pulse height analyzing section 2 to count the pulse in response to the particle size classification, a memory section 21 for storing a relational expression between the direct current level output from the photoelectric converter 9 when no particles exist at the time of shipment or production, and the occurrence frequency of the false counts, and a subtraction section 22 for carrying out an operation process so as not to increase the count value of a peak value corresponding to the minimum particle size among the number of counts output from the counter section 10 by the occurrence frequency of the false counts.

Further, the subtraction processing section 22 is adapted to receive the direct current level output from the photoelectric converter 9 as well as the output signals of the counter section 10. Since the component elements with the same reference number as in the first embodiment shown in FIG. 1 have the same function, further description is omitted.

The embodiments of the present invention refer to the application of the particle counter used with a light scattering method, but the present invention can also be applied to a particle counter used with a light extinction method.

Figure 4A:
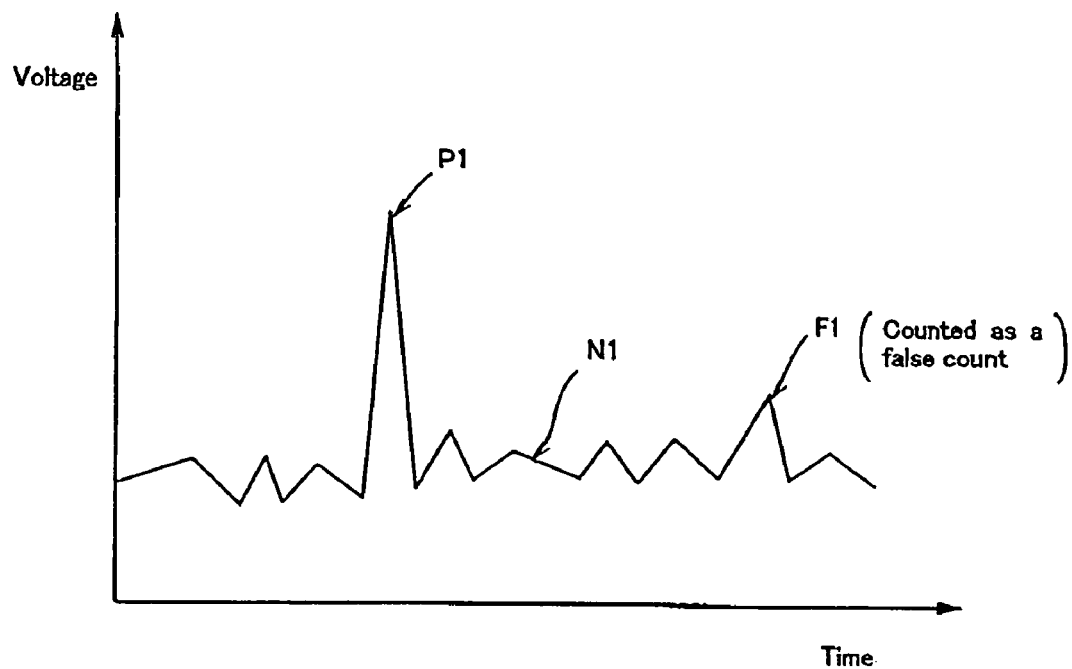
FIG. 4a shows a case of a light scattering method and FIG. 4b shows a case of a light extinction method.

As shown in FIG. 4a, the direct current level N1 by the background light always appears on an output voltage wave form of the photoelectric converter 9 in the particle counter of the light scattering method. The noise of a laser beam La, the noise of the photoelectric converter 9 and the like are superimposed on this direct current level N1. Once particles appear, a pulse P1 appears on the plus side projecting from the direct current level N1. In the case where a peak value of the noise superimposed on the direct current level N1 is equivalent (corresponds) to a peak value corresponding to the minimum particle size, for example, the pulse F1 is counted as a false count.

Figure 4B:
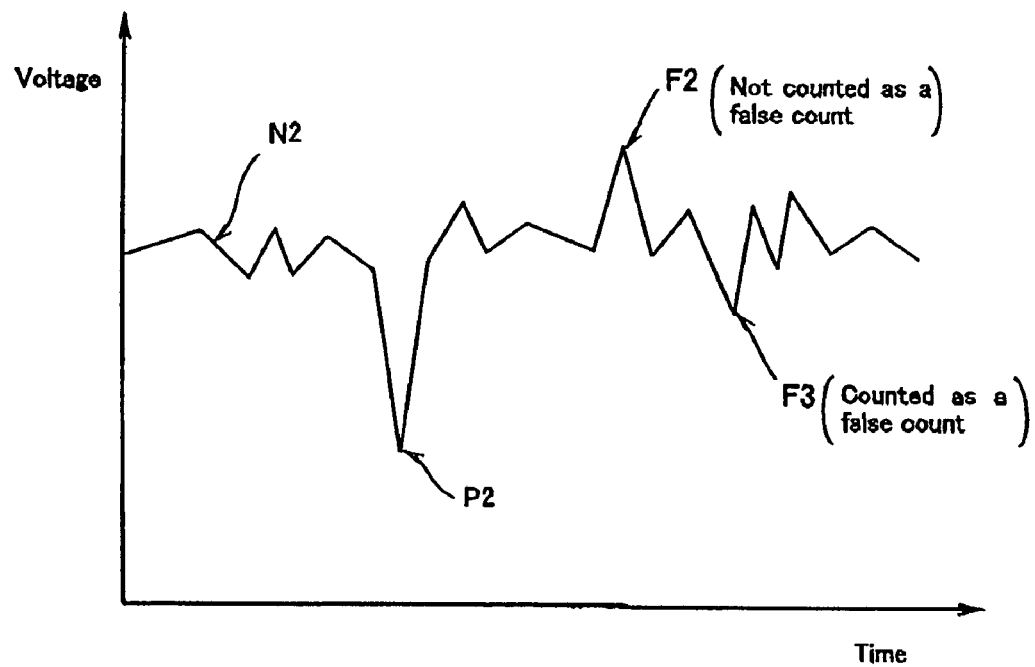

Further, as shown in FIG. 4b, the direct current level N2 by the light irradiated by the light source always appears on an output voltage wave form of the photoelectric converter in the particle counter of the light extinction method. The noise of the light source light, the noise of the photoelectric converter 9 and the like are superimposed on this direct current level N2. Once the particles larger than the minimum particle size appear, a pulse P2 appears on the minus side projecting from the direct current level N2. The peak value, for example, the pulse F2, of the noise superimposed on the direct current level N2, on the plus side is not counted, but in the case where the peak value of the noise superimposed on the direct current level N2 on the minus side is equivalent to the peak value corresponding to the minimum particle size, for example, a pulse F3 is counted as a false count.

A phenomenon as an object of a false count appears as a comparatively small peak of the degree generally corresponding to the minimum particle size. Accordingly, the subtraction process is directed to the peak value corresponding to the minimum particle size for the particle counter. In this manner, even though the peak value corresponding to a particle size larger than the minimum particle size is detected, such a peak value is not regarded as a false count and is not directed to the subtraction process.

To find the occurrence frequency of the false counts, the particle counter is caused to operate, for example, for 24 hours, in the condition in which the particles are not detected, in the use conditions at the time of shipment or production. In such a condition, a discrete value of the peak value corresponding to the minimum particle size is found. The occurrence frequency for the time can be found by dividing the discrete value of the peak value corresponding to the minimum particle size by the operating time. The direct current level D0 of the photoelectric converter 9 and the occurrence frequency m0 of the false counts become a parameter. The unit of occurrence frequency m0 is a "piece/minute" for convenience of explanation.

The occurrence frequency m of the false counts depends on the direct current level D of the photoelectric converter 9. This direct current level D and the level of scattered light Ls emitted by particles in the particle detecting area are proportional to the intensity of a laser beam La. If the intensity of the laser beam La is halved, the direct current level D of the photoelectric converter 9 and the level of the scattered light Ls emitted by the particles are also halved. However, the level of noise etc. resulting from the photoelectric converter 9 remains unchanged. Accordingly, if the intensity of the laser beam La is lowered, in other words, if the direct current level D of the photoelectric converter 9 is lowered, the noise and the like resulting from the photoelectric converter 9 relatively become marked. In other words, if the direct current level D is low, the occurrence frequency m of the false counts becomes higher.

To find the relationship between the occurrence frequency m of the false counts and the direct current level D of the photoelectric converter 9, for example, the occurrence frequency of the false counts in the direct current level, several ways can be found as described above by changing the direct current level D of the photoelectric converter 9. Since these relationships can be presumed to be a straight line (a linear expression), if a vertical axis is the occurrence frequency m of the false counts and a horizontal is the direct current level D of the photoelectric converter 9, the occurrence frequency of the false counts in the two different direct current levels can be found, wherein the straight line (m=aD+b) at an inclination a passing through these two points can be found. If a constant b is found by using the direct current level DO and the occurrence frequency m0, b=m0−aD0.

In this manner, the relational expression between the occurrence frequency m of the false counts and the direct current level D of the photoelectric converter 9 becomes m=aD+m0−aD0, as shown in FIG. 5. These parameters a, m0 and D0 are stored in the memory section 11. These parameters a, m0 and D0 are read out at the time of commencement of measurement and used in the subtraction process by the subtraction section 12.

Operation of the particle counter, as constructed above, according to the second embodiment of the present invention will now be described with reference to a flow chart as shown in FIG. 6.

First, when measurement is commenced, in SP11, the subtraction processing section 22 reads out from the memory section 21 the inclination a, the occurrence frequency m0 of the false counts, and the direct current level D0 of the photoelectric converter 9 at that time, showing the relationship between the occurrence frequency m of the false counts and the direct current level D of the photoelectric converter 9, which have been found and stored in advance.

Next, in SP12, the direct current level D1 of the photoelectric converter 9 at the time of commencement of measurement is measured, and in SP13, the occurrence frequency m1 of the false counts corresponding to the direct current level D1 of the photoelectric converter 9 is calculated using the parameters a, m0 and D0 read out from the memory section 21.

In SP14, the subtraction process is carried out by delimitating the measuring time by the time section (segment) of a reciprocal number 1/m1 of the occurrence frequency m1 of the false counts. This means that "1" is subtracted every 1/m1 hours relative to a discrete value of the minimum particle size output from the counter section 10. However, the subtraction process is not carried out in the first time interval (0-½m1), and the discrete value of the counter section 10 is directly output to the display/output section 4 as the measuring results.

After ½m1 hours have lapsed since commencement of measurement, "1" is subtracted every 1/m1 hours. In the case where the subtraction process is not carried out in the time interval, the number to be subtracted is carried over to the following time interval for accumulation.

For example, when the signals for increasing the discrete value are input to the counter section 10, the counter section 10 counts the signals. However, in the subtraction processing section 22, if the signals are the count value corresponding to the minimum particle size, a process so as not to increase the discrete value by the number to be subtracted is carried out. As a result, this brings about the same effect as the subtraction.

In this manner, more precise discrete value can be obtained by finding the direct current level D0 of the photoelectric converter 9 and the occurrence frequency m0 of the false counts under the use conditions at the time of shipment or production, regarding the relationship between the occurrence frequency m of the false counts and the direct current level D of the photoelectric converter 9 as a linear expression, changing the direct current level D of the photoelectric converter 9 several ways, finding the inclination a, calculating the occurrence frequency m of the false counts from the direct current level D of the photoelectric converter 9 even in the different use conditions, and carrying out the subtraction process.

Next, steps of the subtraction process in a certain time interval of the measuring time are described with reference to a flow chart as shown in FIG. 7. This flow chart shows the subtraction processing steps in the case where the number to be subtracted is carried over from the previous time interval. These subtraction processing steps are common to the first and second embodiments of the present invention.

First, in SP21, the number to be subtracted in the time interval is found by adding the over-carrying number of the number to be subtracted from the previous time interval. In SP22, the subtraction sections 12, 22 judge whether or not the signals for increasing the discrete value are generated. If the signals for increasing the discrete value have been generated, the program proceeds to SP23. If the signals for increasing the discrete value have not been generated, the program proceeds to SP26.

Next, in SP23, it is judged whether or not the number to be subtracted in the time interval was subtracted. If the number to be subtracted in the time interval has not been subtracted, the program proceeds to SP24, wherein the signals generated for increasing the discrete value are not counted. On the other hand, if the number to be subtracted in the time interval has been subtracted, the signals for increasing the discrete value which has been generated as usual are counted in SP25.

In SP26, it is judged whether or not the time interval has ended, that is, 1/m1 hours have lapsed. If the 1/m1 hours have lapsed, the program proceeds to SP27. If 1/m1 hours have not lapsed, the program returns to SP22.

In SP27, it is judged whether or not the number to be subtracted in the time interval has been used up. If the number to be subtracted in the time interval has been used up, the subtraction process in the time interval is completed. On the other hand, if the number to be subtracted in the time interval has not been used up, a process for carrying over the number to be subtracted to the following time interval is carried out in SP28 before ending the subtraction process in the time interval.

EFFECTS OF THE INVENTION

As described above, according to the first aspect of the present invention, it is possible to control the influence of false counts within a certain range by grasping the occurrence frequency of the false counts and as a result, a more precise discrete value can be obtained.

According to the second aspect of the present invention, it is possible to grasp the occurrence frequency of the false counts taking the change of use conditions in mind and as a result, a more precise discrete value can be obtained by controlling the influence of the false counts within a certain range.

According to the third aspect of the present invention, if signals for increasing the discrete value in a certain time interval are not generated, the number to be subtracted is carried over to the following time interval. In this manner, if the signals for increasing the discrete value are not generated, the subtraction process is not carried out and thus, a situation so that the discrete value which has already been displayed is subtracted does not occur.

INDUSTRIAL APPLICABILITY

According to the present invention, it is possible to grasp the occurrence frequency of the false counts bearing the change of use conditions in mind and to provide a particle counter which can provide a more precise discrete value by controlling the influence of false counts within a certain range.

Further, it is unnecessary for users to subtract the false counts, which have been explicitly stated in advance in a specification and the like, from the discrete value of the measurement results and as a result, usability of the particle counter improves.

Although there have been described what are the present embodiments of the invention, it will be understood that variations and modifications may be made thereto within the scope of the claims appended hereto.

What is claimed is:

1. A particle counter for measuring the number of floating particles contained in a sample to determine the particle concentration therein comprising:
    a photoelectric converter which converts light indicative of a sample containing particles in a detection area into a voltage corresponding to an intensity of the light;
    a memory section which stores a frequency of occurrence of pre-calculated false counts; and
    a subtraction section which subtracts a value based on the frequency of occurrence (m) of false counts previously stored in the memory section from a discrete value at a minimum time interval after commencement of measurement;
    wherein the frequency of occurrence (m) of false counts is determined as a reciprocal number $1/m$ at the minimum time interval, and the value is subtracted at each successive occurrence of the minimum time interval during a measuring time.

2. The particle counter according to claim 1, wherein if signals for increasing the discrete value in a certain time interval are generated, the subtraction section subtracts the number to be subtracted from the discrete value, while, if the signals for increasing the discrete value are not generated, the subtraction section carries the number to be subtracted over to a following time interval.

3. A particle counter for measuring the number of floating particles contained in a sample to determine the particle concentration therein comprising:
    a photoelectric converter which converts light indicative of a sample containing particles in a detection area into a voltage corresponding to an intensity of the light; a memory section which stores a relational expression between a direct current level output from a particle detecting section when no particles exist, and a frequency of occurrence of false counts; and
    a subtraction section which determines the frequency of occurrence (m) of false counts corresponding to a direct current level output from the particle detecting section at the time of commencement of measurement with reference to the relational expression previously stored in the memory section, and subtracts a value based on the frequency of occurrence (m) of the false counts from a discrete value at a minimum time interval after commencement of measurement;
    wherein the frequency of occurrence (m) of false counts is determined as a reciprocal number $1/m$ at the minimum time interval, and the value is subtracted at each successive occurrence of the minimum time interval during a measuring time.

4. The particle counter according to claim 3, wherein if signals for increasing the discrete value in a certain time interval are generated, the subtraction section subtracts the number to be subtracted from the discrete value, while, if the signals for increasing the discrete value are not generated, the subtraction section carries the number to be subtracted over to a following time interval.

* * * * *